US009575031B2

(12) United States Patent
Vulto et al.

(10) Patent No.: US 9,575,031 B2
(45) Date of Patent: Feb. 21, 2017

(54) APPARATUS AND PROCESS FOR DEPLETION ZONE ISOTACHOPHORESIS

(71) Applicant: UNIVERSITEIT LEIDEN, Leiden (NL)

(72) Inventors: Paul Vulto, Leiden (NL); Thomas Hankemeier, Leiden (NL); Jos Quist, Leiden (NL); Kjeld Janssen, Leiden (NL)

(73) Assignee: Universiteit Leiden, Leiden (NL)

(*) Notice: Subject to any disclaimer, the term of this patent is extended or adjusted under 35 U.S.C. 154(b) by 0 days.

(21) Appl. No.: 14/422,736

(22) PCT Filed: Aug. 21, 2013

(86) PCT No.: PCT/NL2013/050608
§ 371 (c)(1),
(2) Date: Feb. 20, 2015

(87) PCT Pub. No.: WO2014/030997
PCT Pub. Date: Feb. 27, 2014

(65) Prior Publication Data
US 2015/0219594 A1 Aug. 6, 2015

Related U.S. Application Data

(60) Provisional application No. 61/691,560, filed on Aug. 21, 2012.

(51) Int. Cl.
*G01N 27/447* (2006.01)

(52) U.S. Cl.
CPC ...... *G01N 27/447* (2013.01); *G01N 27/44773* (2013.01)

(58) Field of Classification Search
CPC ............ G01N 27/447; G01N 27/44773
See application file for complete search history.

(56) References Cited

U.S. PATENT DOCUMENTS

| 3,869,365 A | 3/1975 | Sunden |
| 2005/0121324 A1 | 6/2005 | Park et al. |
| 2010/0155241 A1 | 6/2010 | Ross et al. |

OTHER PUBLICATIONS

Quist et al., "Single-Electrolyte Isotachophoresis Using a Nanochannel—Induced Depletion Zone" Analytical Chemistry 83(20):7910-7915 (2011).
Quist et al., "Depletion Zone Isotachophoresis: A New Micro/Nanofluidic Electrokinetic Method" 14th International Conference on Miniaturized Systems for Chemistry and Life Sciences, Oct. 1, 2010, p. 1636, Paragraph 4.

*Primary Examiner* — J. Christopher Ball
(74) *Attorney, Agent, or Firm* — Nixon Peabody LLP

(57) ABSTRACT

The present invention relates to a method and an apparatus for concentrating, detecting and/or isolating a plurality of charged analytes contained in a sample by depletion zone isotachophoresis.

19 Claims, 10 Drawing Sheets

APPARATUS AND PROCESS FOR DEPLETION ZONE ISOTACHOPHORESIS

CROSS-REFERENCE TO RELATED APPLICATIONS

This application is a 35 U.S.C. §371 National Phase Entry Application of International Application No. PCT/NL13/050608 filed Aug. 21, 2013, and which claims benefit of U.S. Provisional Application Ser. No. 61/691,560 filed Aug. 21, 2012 the contents of which are incorporated herein by reference in their entireties.

TECHNICAL FIELD OF THE INVENTION

The present invention generally relates to the field of analytical electrophoresis systems and methods. More specifically, this invention focuses on highly selective isotachophoresis and electrokinetic transport for the extraction of charged molecules, and a method for assessing the position of a focused analyte zone that is created by means of depletion zone isotachophoresis, by positioning at least part of the zone or an adjacent or positionally linked zone in front of a sensing element. The method thus relates to an apparatus and a method for concentrating, separating and/or isolating a plurality of charged analytes contained in a sample by depletion zone isotachophoresis.

BACKGROUND OF THE INVENTION

The comprehensive analysis of low-abundance analytes in ultrasmall volumes of complex biological matrices—including samples from single cells—is one of the main challenges of today's science and technology. To address this challenge, efficient concentration and separation techniques are critically needed.

Concentration polarization is a well known phenomenon in which part of a liquid is depleted of ions. For the transport and separation of charged molecules in capillaries and microchannels, electrophoresis is often employed and has found widespread applications. However, the sensitivity and selectivity to accurately handle and separate substances in tubing is limited, thus requiring efficient sample preconcentration methods.

For ionic analytes, isotachophoresis (ITP) has proven as a powerful candidate, as disclosed by B. Jung et al., Analytical Chemistry, vol. 78, pp. 2319-2327, (2006); R. B. Schoch et al., Lab on a Chip, vol. 9, pp. 2145-2152, (2009).

ITP uses an imposed electrophoretic mobility gradient to create concentrated analyte zones with non-dispersing interfaces in an elongated channel. Analyte ions to be stacked and separated are typically introduced between a leading and a trailing electrolyte with an effective mobility respectively higher and lower than those of the analytes. Under the influence of an electric field, analyte ions redistribute themselves into sequential zones in order of reducing effective mobility, starting from the leading, and ending with the trailing electrolyte. ITP based separations typically result in adjacent, contiguous zones of analytes moving at identical speed downstream in a main separation channel.

Use of isotachophoresis for separation and detection of charged components typically requires additional steps, typically also involving a secondary separation method. Examples include pre-concentration of compounds by isotachophoresis followed by electrophoresis and analysis, as disclosed in US-A-2006/0254915, US-A-2002/0189946; isotachophoresis followed by zone electrophoretic separation.

Transient isotachophoresis (tITP) couples the concentration characteristics of isotachophoresis with the resolving power of zone electrophoresis. However, tITP is of significant complexity, as it requires injection of three electrolyte zones (background electrolyte, sample, background electrolyte) and the moment of transience is difficult to monitor.

Furthermore, to be effective, tITP may require the use of a electrolytes with specific chemical and physical properties, as exemplified in U.S. Pat. No. 5,817,225 and WO-A-2009/079028.

Accordingly, there remains a need to separate multiple compounds in complex samples, without the need to operate with different electrolytes, and with the potential to not only detect and analyse components, but also to selectively separate the components.

SUMMARY OF THE INVENTION

Accordingly, in a first aspect, the present invention relates to a method for concentrating, separating and/or isolating a plurality of charged analytes contained in a sample by depletion zone isotachophoresis, in an apparatus comprising at least a main separation channel (C) comprising an electrolyte, the channel (C) comprising a downstream end (D) and an upstream end (U), and a depletion zone formation means (N) placed in or connected to an intermediate region between the upstream end and the downstream end, the method comprising the steps of: introducing the sample into the electrolyte at an upstream channel region adjacent to the upstream end (U), and forming and/or maintaining an ion depleted zone in the separation channel (C) and adjacent to the depletion zone formation means at a depletion rate (R) using the depletion zone formation means, and applying an electric field ($\hat{E}1$) between the downstream end (D) and the upstream end (U) and applying a downstream fluid flow (F), thereby causing focussing and separation of the analytes forming respective focused analyte zones in the separation channel (C) and adjacent to the ion depleted zone, and optionally detecting the position and/or composition of the focused zones, and adjusting fluid flow (F) and/or depletion rate (R) to move at least one focussed analyte zone in a upstream and/or downstream direction and/or position the one or more focussed analyte zones at a desired position in the separation channel (C).

In a further aspect, the subject invention relates to the use of an apparatus according to the present invention for the separation of analytes in a sample by depletion zone isotachophoresis. Further aspects of the invention are embodied in the claims.

BRIEF DESCRIPTION OF THE FIGURES

These and further features can be gathered from the claims, description and drawings and the individual features, both alone and in the form of sub-combinations, can be realized in an embodiment of the invention and in other fields and can represent advantageous, independently protectable constructions for which protection is hereby claimed. Embodiments of the invention are described in greater detail hereinafter relative to the drawings, wherein:

FIG. 1(a) shows the setup consisting of a microchannel and perpendicular nanochannel; FIG. 1(b) shows the nanochannel induces an ion-depleted zone inside the microchannel; FIG. 1(c) shows an electric field over the microchannel results in separation of charged analytes into distinctive zones.

FIG. 3 (b) discloses a CCD image of an example of dzITP separated zones. The channel contains a depletion zone that extends mostly in the downstream channel. Analytes focus at the border of the depletion zone and order themselves in clearly distinguishable zones. Lines that indicate micro- and nanochannels are drawn onto the CCD image.

FIG. 5 (a) discloses a layout with an example of applied voltages and currents for tuneable filtering. FIG. 5 (b) shows CCD images showing the part of the separation channel near the nanochannel junction. With increasing currents, a focused zone of fluorescein becomes increasingly released. FIG. 5 (c) discloses an inset showing two laminar streams: depleted fluid from the nanochannel and fluorescein-containing fluid from the dzITP-separation. The two fluid streams are mixed rapidly downstream from the nanochannel.

FIG. 6(a): Focusing and separation of fluorescein and 6-carboxyfluorescein at several voltage magnitudes. FIG. 6(b): Dependence of focusing strength on the voltage magnitude. Focusing strengths are represented by the steepness of the slopes between the fluorescein plateau and the depletion zone; voltage magnitudes are represented by the upstream voltage. FIG. 1(c): Distances of the edge between the depletion zone and the fluorescein zone from the nanochannel. Measurements were triplicated and randomized.

FIG. 9(a): Completed dzITP-separation of a discrete injection of fluorescein, FITC-leucine, 6-carboxyfluorescein and FITC-glutamate. FIG. 9(b) Release of the fluorescein zone. FIG. 9(c) Retained zones after fluorescein release. c) Release of the FITC-leucine zone. FIG. 9(d) and FIG. 9(e) show retained zones after fluorescein and FITC-leucine release.

DETAILED DESCRIPTION OF THE INVENTION

Figure 1:
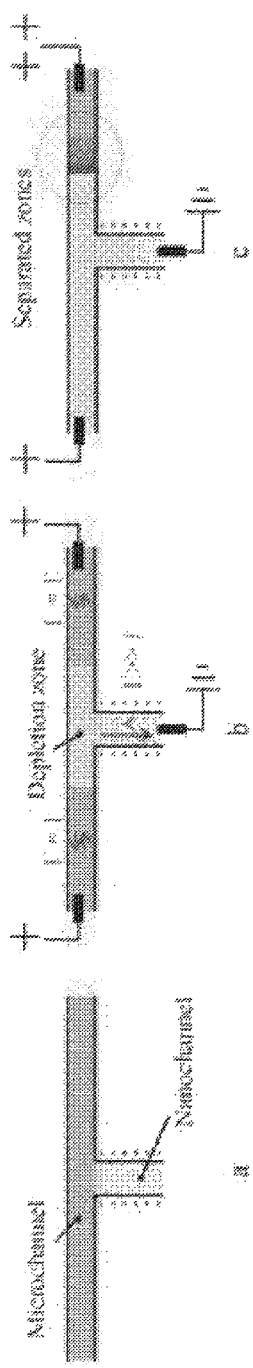
FIG. 1(a) to (c) disclose schematic deplictations of a preferred embodiment device according to the invention, indicating the principle of depletion zone isotachophoresis.

The present invention relates to depletion zone isotachophoresis, which synergetically combines the strengths of on-chip ITP with the merits of nanofluidic concentration devices. Methods and apparatus of this invention may advantageously be used in several fields such as diagnostics, life science, biodefense, food and water industries, and agricultural and environmental sensing. Analytes to be separated may include charged molecules such as amino acids, peptides, proteins, glycoproteins, biomarkers, hormones, metabolites, organelles, membranes, liposomes, lipids, saccharides and derivatives thereof, antibodies, antibody complexes, nucleic acids, nucleic acid-protein complexes, food additives, pathogens, viruses, drugs, heavy metals, toxins, toxic industrial chemicals, explosives, chemical weapons, biological weapons, ions, and/or the like.

In order to process an analyte zone of interest, the position needs to be precisely assessed In order to assess the position of an analyte zone, preferably a sensing element is employed, such as a laser, electrodes, other (temperature), CMOS sensor etc. However, the analyte zone of interest needs to be within reach of the sensor, or alternatively, the analyte zone of interest needs to be related to a second zone that is within reach of the sensor. The invention therefore preferably comprises a method for positioning an analyte concentration zone, such that its width and position can be determined. The method preferably comprises (I) creation an ion depleted zone, (II) focussing of analytes at the border of that zone; (III) separating analytes in multiple zones according to isotachophoretic principles, and (IV) tuning the balance of the flow through the focusing channel and the ion depletion flux such that the analyte zone or its related zones are positioned in the sensing area.

Under applying voltage across a nanochannel, nanojunction or an ion permeative-selective membrane, the so called "ion concentration polarization (ICP)" phenomenon occurs around the membrane or channel/junction.

ICP thereby refers to an electrochemical transport phenomenon wherein an ion concentration becomes polarized across the membrane. In the case of cation selective membrane, when voltage is applied, the ion concentration would decrease around the anodic side of the membrane and increase around the cathodic side of that. Those two regions are referred to as "ion depletion zone" and "ion enrichment zone", respectively.

The invention further preferably also relates to a method to determine the growth rate of an analyte zone; and/or to determine the leakage rate of an analyte zone along the depletion zone; and to determine the mobility of an analyte zone; to a method for transporting a selected analyte zone away, and to the use of spacer compounds, and its use to determine reaction constants and products.

The method may be beneficially operated either by keeping the depletion flux constant, and varying the flow of analytes; or keeping the analyte flow constant, while varying the depletion rate, i.e. stopping the depletion rate. Either method permits to determine the position of the depletion zone.

In a further aspect of the present invention, device actuation may be performed based on algorithmic analysis of detector signals, for instance by a feedback loop between actuation of a dzITP device and detection of dzITP marker compound zones. For actuation any method may be used that shifts the balance between fluid flow and depletion zone formation, including changes of applied currents, electric fields, voltages and/or pressures. This actuation preferably results in positioning of the marker compound zones.

If a single point detector is to be employed, a suitable algorithm may be employed to determine whether or not a dzITP zone of a marker compound is present at the detector position.

In this case, the actuation of the dzITP device may be changed periodically, moving the marker compound zone back and forth, resulting in alternating presence and absence of the marker compound zone at the detector position. If the periods of these alterations are short, this will lead to an approximately stable position of the marker zone edge.

If two or more point detectors are used, the algorithm/feedback loop can be used to stabilize marker zone edges within channel sections between the detection points.

If detectors are used that can create line scans or images, the precise positions of one or multiple marker zones can be determined and stabilized.

The sample containing the analytes may be a clinical sample derived from a body fluid or tissue sample, or it can be from an environmental source, for example.

Further, the analyte to be extracted may be an extract to sampled derived from an immunoassay, protein sequencing, mass spectrometry, gels, PGR, isothermal amplification, hybridization reactions, microarrays, protein-DNA binding.

A sample may be treated with a lysing buffer if the analyte molecules are contained in cells, releasing the analytes into solution for subsequent processing.

Electrocapture herein refers to a method which utilizes capillaries with perm-selective membrane junctions for trapping and localisation. The present invention employs an apparatus comprising a main separation channel (C) comprising a proximal end (P) and a distal end (D), and a concentration polarization means (N) placed in an intermediate region between the proximal end and the distal end.

The concentration polarization means, which may also be referred to as the depletion zone formation means, according to the invention may be any means that allows generating the concentration polarization. Preferably, the concentration polarization means is a nanochannel, i.e. a channel with an average diameter in the nanometer range.

Within nanochannels, ion distribution of counter- and co-ions, as defined relative to the surface charge, may be affected significantly by wall surface charge. When an electric field is applied over such a nanochannel, the current carries electrolyte counter- and co-ions asymmetrically, resulting in concentration polarization.

For instance, for glass channels having a negative surface charge, this results in ion depletion at the anodic entrance of the nanochannel, and ion enrichment at the cathodic entrance.

In devices consisting of two parallel microchannels connected by a nanochannel, see FIG. 1, a bulk flow through the microchannel promotes the growth of the depletion zone downstream to the nanochannel, while upstream its growth is limited. This bulk flow might be an electro-osmotic flow (EOF), a pressure-driven flow, or a combination of these. Under appropriate conditions, the upstream border of the depletion zone can have a very stable position over time, thus becoming quasi-static.

Figure 2:
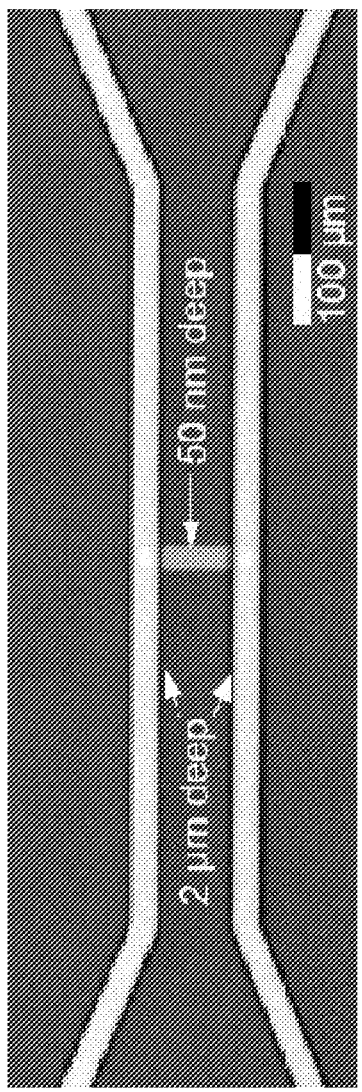
FIG. 2 discloses a micrograph of a part of a chip comprising a separation channel comprising a nanochannel connecting two microchannels.
Figure 3:
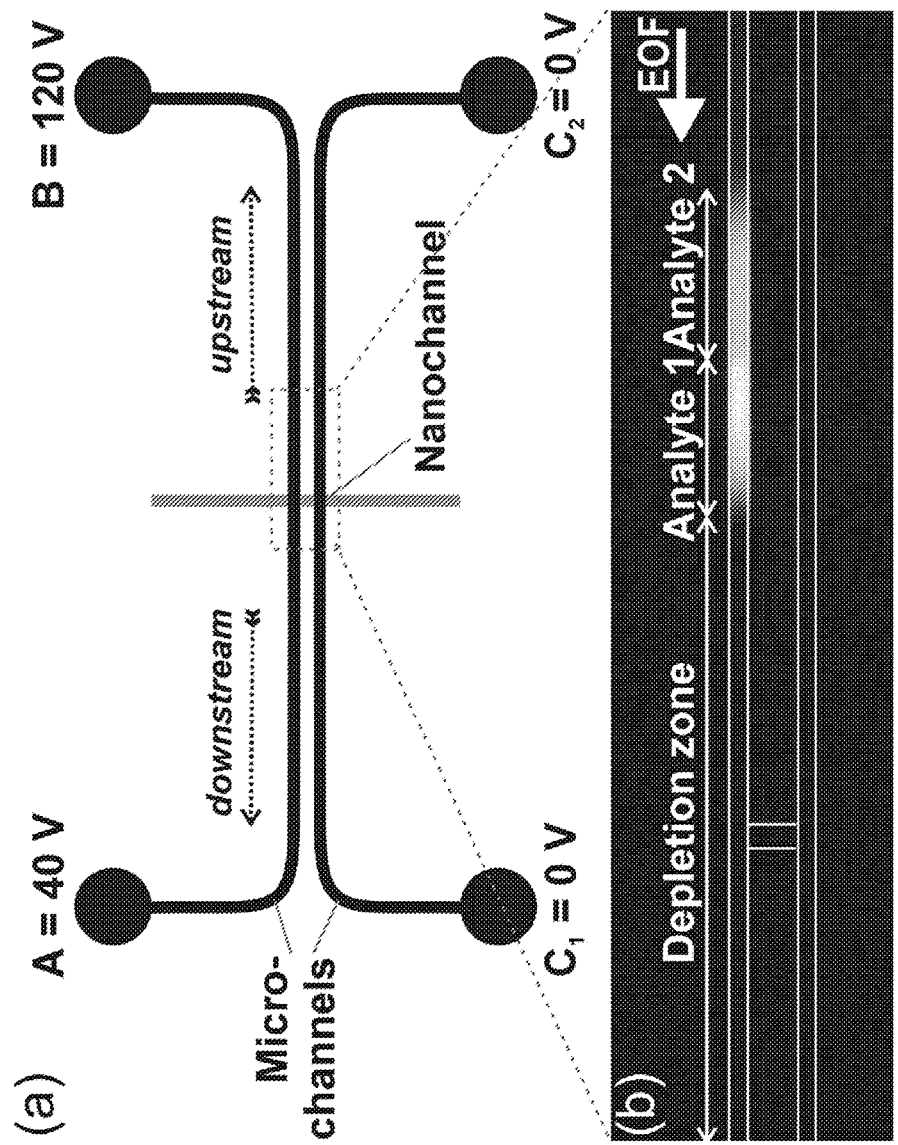
FIG. 3 (a) discloses a chip layout consisting of two microchannels and one nanochannel, showing an example of three-point voltage actuation is provided: A is the downstream voltage and B the upstream voltage, while the lower channel is connected to ground, as represented by voltages $C_{1,2}=0$ V. Downstream and upstream directions are indicated by dashed arrows.

In a preferred embodiment of the apparatus according to the invention, at least two parallel microchannels are connected by a nanochannel, over which an electric field is applied, see for instance FIGS. 1, 2 and 3 (a). Asymmetric distribution of anions and cations makes the nanochannel perm-selective, and thus leading to concentration polarization. This causes the formation of a depletion zone in the anodic microchannel. A tangential electro osmotic flow (EOF) through this microchannel transports analytes toward the border of the depletion zone, where they are trapped (FIG. 3b).

The border of the depletion zone is a concentration gradient and therefore gives rise to a gradient in electric field. On this gradient, co-ions, e.g. anions in the case of glass channels, can be focused efficiently. Given that the upstream border of the depletion zone has a stable position over time, the focusing of a co-ion occurs at a position on the gradient where its net velocity becomes zero. This net velocity $v_{i,net}$, is the result of a sum of bulk flow and opposite electrophoretic transport according to general formula (I):

$$v_{i,net}=v_{bulk}+\mu_i E \quad (I)$$

Wherein $v_{bulk}$ is the bulk flow velocity (which naturally is independent of local electric field), $m_i$ the electrophoretic mobility of co-ion i, and E is the electric field. Thus, a co-ion will focus at a location where the electric field is such, that its electrophoretic velocity equals the bulk flow velocity ($v_{i,net}=0$). Co-ions with different mobility will focus at different positions on the electric field gradient, as depicted in FIG. 2. During focusing, analytes may reach concentrations which are dominant compared to the background electrolyte concentration, resulting in isotachophoretic separation and plateau formation. This is referred to as "depletion zone isotachophoresis (dzITP)".

In dzITP, further focusing typically results in broadening plateaus, see FIG. 2 at the right side, until all co-ions are ordered in adjacent zones according to their mobility.

This process differs from the generally known isotachophoresis (ITP), in that in ITP, analytes are sandwiched between a high-mobility leading electrolyte and a low-mobility trailing electrolyte. An ITP-separation also results in the focusing of analytes towards a plateau concentration, and an ordering in adjacent zones according to ionic mobility. However, in dzITP the depletion zone replaces the trailing electrolyte.

The present process may be operated under plateau mode, i.e. when the charged analyte molecules are present at sufficiently high initial concentration to form focused zones with a plateau concentration profile at steady state.

Alternatively, for low initial concentrations and short focusing times of charged analytes, the zone width can be on the order of the interface width, also referred to as peak mode, where concentration profiles of the focused zones are approximately Gaussian rather than plateau shaped. In peak mode, spacer molecules may be used to separate analytes with different ionic mobilities.

The interface width in peak mode ITP is governed by the electric field gradient.

The electrolyte preferably has a pH suitable with respect to the isoelectric points of the analyte molecules. The pH value of the electrolyte is selected such that all analyte molecules are either negatively or positively charged, typically having a pH value between 3 and 10.

Further, the pH value and concentration can be chosen such that contaminating molecules and analyte molecules have different effective electrophoretic mobilities.

Preferably, an electro-kinetic or pressure-driven flow is applied along the extraction channels, crossing the main separation channel, and therefore injecting the focused analytes into the extraction channel. This transfer process is only applied briefly until the analyte zones are inside the extraction channels. The extraction purity and yield can be increased by optimizing the widths of the extraction channels at the cross or integrating shaping electrodes to optimize the electric field or flow lines.

Then, the electric field along the main separation channel may advantageously be reapplied to transport further charged molecules in this channel to extraction channel, or to a waste reservoir. Subsequently, the fluid flow through the extraction channel is reinitiated to transport the analyte molecules into the extraction reservoir, which are preferably located at the end of the channels.

In a one embodiment, the sample may be introduced into the main separation channel between the proximal channel region and distal channel region through specific injection channels.

In another preferred embodiment, the sample may comprise spacer compounds. In this case, applying an electric field along the main separation channel preferably results in the bracketing of analytes by predefined spacers, preferably at least two, one upstream and one downstream. The analytes and spacers may be selected such that they are preconcentrated and separated in alternating and adjacent zones.

The electrolyte chemistry of the spacers is preferably conceived such that the composition, ionic strength, and pH value lead to plateau mode ITP with predefined lengths of the plateaus. In contrast, the analytes are typically focused in peak mode ITP because they are present at lower concentrations.

Due to the known or measured plateau lengths of a spacer, the distance between the individual analytes may be set, and these distances typically correspond to the flow require to move a certain analyte band to the extraction channels, and preferably controlled by the detection of the focused zones.

The analytes may advantageously be collected after separated by isotachophoresis. According to one embodiment, a transversal flow is applied carried until an analyte has reached a collection zone located at an end of the extraction part of the respective extraction channel (E). According to another embodiment, the step of applying a transversal flow is interrupted when an analyte has accumulated in a zone of the respective extraction channel (E) displaced from the main separation channel (C), preferably followed by a step of reapplying the electric field and thus causing further analyte present in the main separation channel (C) to move forward towards the distal end (D), followed by switching off the electric field (E) and reapplying the transversal flow until this analyte as reached a collection zone located at the distal end of the extraction part of the extraction channel (E).

In addition, the analytes can be extracted into an extraction buffer (EB) that is different from the electrolyte.

According to an advantageous embodiment, the means for detecting focused zones may comprise electrodes arranged in the main separation channel (C) and/or in the extraction channel (E) and/or in the collection zone.

The present invention also provides systems and methods for robust and repeatable extractions of at least one specific analyte from a complex sample. The analytes are preferably separated at a given distance from each other, and these charged species are focused in a microchannel. The thus preconcentrated and self-focused analyte zones travel downstream, and once they arrive at their predetermined site as being continuously controlled, they are all subsequently transferred into an extraction channel by an applied fluid flow perpendicular to the main separation channel. The analytes may then be dispensed into reservoirs, and/or typically subjected to detailed analysis, or they may isolated further to achieve increased extraction purities.

The present method advantageously allows the realization of miniaturized, portable, and automated sample preparation modules, which can be integrated in instruments for point-of-care diagnostics, life science, biodefense, food and water industries, and agricultural and environmental sensing. In addition, these instruments can be manufactured cost-effectively, being of interest to the drug discovery industry and R&D labs working with gel electrophoresis. For such application fields, the method may be employed for the separation of proteins from nucleic acids, the fractionation of proteins by size or charge, or the fractionation of nucleic acids by length, for example.

The methods, apparatus and required electrolytes can be provided as a kit for carrying out separation, preconcentration and isolation of analytes, wherein the apparatus includes disposable or semi-disposable microfluidic devices with integrated channels. For dispatching purposes, these channels can be dry, prefilled with custom electrolytes at the final concentration or as a concentrated stock solution, or the electrolytes can be present in a lyophilized form. The electrolytes can be provided as prefilled amounts for one or multiple measurements. This allows the user to perform measurements on the field, in the lab or anywhere else by adding the required amount of custom electrolytes or water.

Isotachophoretic separations are triggered at the border of a nanochannel-induced ion-depleted zone. This depletion zone acts as a terminating electrolyte and is created by concentration polarization over the nanochannel. The process is suited for both continuous and discrete sample injections, and separation of up to four analytes was proven. Continuous injection of a spacer compound may advantageously be used for selective analyte elution. Zones were kept focused for over one hour, while shifting less than 700 µm. Moreover, zones could be deliberately positioned in the separation channel and focusing strength could be precisely tuned employing a three-point voltage actuation scheme. This makes depletion zone isotachophoresis (dzITP) a fully controllable single-electrolyte focusing and separation technique. For on-chip electrokinetic methods, dzITP sets a new standard in terms of versatility and operational simplicity.

Isotachophoresis (ITP) is a powerful electrokinetic technique for the concentration, separation, purification, and quantification of ionic analytes, especially when downscaled to microfluidic devices.1,2 In 1998, Walker et al. were among the first to demonstrate on-chip ITP using Raman spectroscopy to detect herbicides, see also Walker, et al, Anal. Chem. 1998, 70, 3766-3769. Kanianski et al., in Anal. Chem. 2000, 72, 3596-3604, coupled ITP to capillary electrophoresis (CE) on a chip and showed isotachopherograms of up to 14 analytes. Several reports describe over 10,000-fold concentration, see for instance Bottenus, D. et al., Lab Chip 2011, 11, 890-898, and Wang, J. et al., Electrophoresis 2009, 30, 3250-3256. Jung et al. even reported million fold sample stacking using transient ITP in Anal. Chem. 2006, 78, 2319-2327. Miniaturized ITP is applicable to a broad range of samples, including toxins from tap water, see Bercovici, M. et al., Anal. Chem. 2010, 82, 1858-1866), explosive residues, Prest, J. E. et al., J. Chromatogr., A 2008, 1195, 157-163., proteins, see Huang, H. et al., Electrophoresis 2005, 26, 2254-2260. DNA from PCR samples, see Liu, D. et al., J. Chromatogr., A 2008, 1214, 165-170; and J. Chromatogr., B 2006, 844, 32-38; nucleic acids from whole blood, see Persat, A. et al. Anal. Chem. 2009, 81, 9507-9511; and small RNA molecules from cell lysate. Schoch, R. B. et al., Lab Chip 2009, 9, 2145-2152.

Hybridization of RNAs with molecular beacons by ITP, as described in Persat, A. et al., Anal. Chem. 2011, 83, 2310-2316 was applied to bacterial rRNAs from urine, see also Bercovici, M. et al., Anal. Chem. 2011, 83, 4110-4117, demonstrating the potential of on-chip ITP for biochemical assays. A major recent achievement was the integration of an ITP chip and laser-induced-fluorescence (LIF) detection into a single handheld device, see Kaigala, G. V. et al., Lab Chip 2010, 10, 2242-2250. Nevertheless, ITP has still to come to its full potential, as until now it has not been widely used for bioanalytical applications, see Ahmed, F. E. J. Chromatogr., B 2009, 877, 1963-1981 and Suntornsuk, L. Anal. Bioanal. Chem. 2010, 398, 29-52. A major limitation is that ITP requires a sample to be injected between a leading electrolyte and a terminating electrolyte. Compared to, e.g., capillary electrophoresis (CE), which uses a single electrolyte only, handling and method development is not straightforward. Another limitation of conventional ITP is that analyte zone positions are difficult to control. This is due to the different conductivities of the ITP zones, resulting in continuous changes of electric field distributions during electromigration. Several stationary ITP strategies have been developed to alleviate this limitation. One such strategy employs a hydrodynamic counterflow, but this has the disadvantage of dispersion due to a parabolic flow profile (see Urbanek, M. et al., Electrophoresis 2006, 27, 4859-4871). A more elegant strategy is balancing the electrophoretic motion of the ITP zones by an opposite electro-osmotic flow (EOF), see Abelev, G. I. et al., Immunol. 1989, 26, 41-47; and Breadmore, M. C. J. Chromatogr., A 2010, 1217, 3900-3906. However, with this method it is still complicated to change analyte zone positions in a controlled manner without changing pH or electrolyte concentrations.

In this paper we overcome the mentioned limitations by a radically different approach which combines the strengths of on-chip ITP with the merits of nanofluidic concentration devices. Wang, Y.-C. et al, Anal. Chem. 2005, 77, 4293-4299; and Kim, S. M. et al., Anal. Chem. 2006, 78, 4779-4785. These devices, which have been extensively reviewed by Kim et al. Chem. Soc. Rev. 2010, 39, 912-922, are in fact miniaturized variants of electrocapture devices. Electrocapture is a powerful method which utilizes capillaries with perm-selective membrane junctions for trapping and selective release of ionic compounds, see also Park, S. R. et al. Anal. Chem. 2003, 75, 4467-4474, and Astorga-Wells, J. et al., Anal. Chem. 2005, 77, 7131-7136. In nanofluidic concentration devices, at least two parallel microchannels are connected by a nanochannel, over which an electric field is applied (FIG. 3a). Asymmetric distribution of anions and cations, see Plecis, A.; Schoch, R. B. et al., Nano Lett. 2005, 5, 1147-1155 and Janssen, K. G. H.; Hoang, H. T.; Floris, J.; de Vries, J.; Tas, N. R.; Eijkel, J. C. T.; Hankemeier, T. Anal. Chem. 2008, 80, 8095-8101, makes the nanochannel perm-selective, leading to concentration polarization, see Pu, Q. et al., Nano Lett. 2004, 4, 1099-1103 and Zangle, T. A. et al., Anal. Chem. 2010, 82, 3114-3117. This causes the formation of a depletion zone in the anodic microchannel. A tangential EOF through this microchannel transports analytes toward the border of the depletion zone, where they are trapped (FIG. 1b).

Various groups have investigated devices based on similar principles, see for instance Zhou, K. et al., J. Am. Chem. Soc. 2008, 130, 8614-8616, or Yu, Q. et al., Microfluid. Nanofluid. 2011, 1-9, showing that this has become a very active research field within a short time. Potential applications include immunoassays, as disclosed in Wang, Y.-C., Lab Chip 2008, 8, 392-394 and Lee, J. H. et al., Anal. Chem. 2008, 80, 3198-3204, enzyme assays, Lee, J. H. et al. above, Sarkar, A. et al., Lab Chip 2011, 11, 2569-2576; massive parallelization, Lee, J. H. et al., Lab Chip 2008, 8, 596-601, or Ko, S. H. et al., Lab Chip 2011, 11, 1351-1358, and desalination, see Kim, S. J. et al., Nat. Nanotechnol. 2010, 5, 297-301. Here we employ a depletion zone to induce isotachophoretic separations. To our knowledge, this is the first time such separations are demonstrated in nanofluidic concentration devices. Depletion zone isotachophoresis (dzITP), as we coin this novel approach, is performed with a single electrolyte only. A three-point voltage actuation scheme gives complete control over the position of the zones and the sharpness of their borders, utilizing the fact that the method is quasi-static.

The simplicity and versatility of our method makes it a powerful new tool in the electrokinetic focusing and separation toolkit.

A preferred embodiment of the subject invention relates to a tunable low-pas filter based on ionic mobility. The micro/nanofluidic filter preferably employs depletion zone isotachophoresis (dzITP) for separation of compounds that are selectively released along the nanochannel-induced depletion zone. Applicants could demonstrate quantitative control of the release of fluorescent compounds through the filter using current and voltage actuation. Two modes of operation are presented. In continuous mode, synchronous supply, focusing, separation and release of compounds preferably yields a filter with tuneable ionic mobility cut-off.

In pulsed mode, individual zone release is preferably controlled by visual feedback. The filter was applied to analyze diluted raw urine to which fluorescein was added for indirect detection of several compounds within a specific ionic mobility window. Tuneable ionic mobility filtering is an important addition to dzITP and a further proof of its versatility and applicability for biochemical assays.

Preferably, controlled filtration is popular amongst sample pre-treatment methods as it is fast and simple to implement.

In the subject case, electrostatic or size-based exclusion is used as a filtering principle. An approach which is less prone to clogging and more interesting from an electrokinetic perspective is the use of a ion-depleted zone, preferably nanochannel-induced. Such a depletion zone can be formed by concentration polarization, a process that occurs upon application of an electric field over perm-selective conduits; that is, inside a nanochannel the surface charge of the walls permits passage of counter ions, but excludes co-ions.

The depletion zone can be maintained at a stable position adjacent to the nanochannel entrance, even if placed in a fluid flow. The high electric field in the depletion zone blocks charged compounds from passing, making such devices suited for highly efficient analyte trapping and water purification applications. Experiments with electrocapture devices, which used nanoporous membranes for depletion zone formation, have indicated that they can be used filters that separate between ionic mobilities. However, this approach is preferably suitable for analytes with rather low mobilities.

The process according to the present invention advantageously permits to focus analytes at the border of an ion-depleted zone and to separate them into adjacent zones, which are ordered according to their ionic mobilities.

By replacing the terminating electrolyte typically employed in ITP by the depletion zone replaces the, dzITP is a single-electrolyte isotachophoretic method, which is an important simplification over conventional ITP. Moreover, dzITP exhibits great versatility, because analyte zones can be precisely positioned by tuning the balance between fluid flow through the separation channel and depletion zone growth.

In a preferred embodiment, the versatility of the dzITP according to the invention is further enhanced by introducing a novel filtering principle that selects compounds based on ionic mobility. This dzITP filter is a tunable low-pass filter, which allows to controllably release analyte compounds along the depletion zone. Ionic mobility cut-offs are preferably established by synchronous isotachophoretic focusing, separation and release of one or multiple focused analyte zones.

The operation for dzITP filtering may be employed indifferent modes. Preferably, it is operated in a continuous mode, or in a pulsed mode, or combinations thereof. In continuous mode, supply and release of compounds are balanced in order to establish an ionic mobility cut-off, preferably aided by a partially released marker compound.

Compounds with lower mobilities than the marker compound may then be co-released with the marker compound; compounds with higher mobilities will be trapped in isotachophoretic zones behind the marker compound zone.

In pulsed mode, the flow rate is temporarily increased to allow one or more individual zones to be released aided by visual feedback control. The device and method according to the invention may advantageously be used for trapping and indirect detection of metabolites from biological samples, e.g. urine using fluorescein as an indirect marker, demonstrating the applicability of dzITP filtering for real-time monitoring and analysis of complex biological samples.

The applications for zone positioning and selective leakage of analyte zones may advantageously be employed for an number of different uses and a great variety of applications, including, but not limited to indirect detection, low abundant compound enrichment, downstream analysis and/ or sensor scanning.

Indirect detection herein relates to the following method: Given a sample containing analytes that are focused and separated in separate ITP zones. A marker molecule is flushed through the zones in order to indirectly visualize the focused analytes. However, too much of this marker molecule would cover the complete readout window, therefore it is important to selectively release the marker molecule while keeping the analytes of interest trapped in their zones. To do this, the release of marker molecules has to be controlled by positioned the first zone of analyte of interest in close vicinity of the depletion zone formation means.

A similar scheme occurs when a labelling reaction is done. In this case a marker molecule is coupled to an analyte of interest. This may be a reporter molecule in e.g. a bioassay. The non coupled molecules need to be removed from the readout window and can therefore be selectively released.

Low abundant compound enrichment: Given a sample containing an analyte of interest that is present in low abundance with respect to other analytes. If focused and separated in ITP zones, the analyte of interest would be not detectable as other analytes would cover the complete readout window. Selective release of analytes that are of no interest allows continuous concentration of the analyte of interest with time while still positioning the analyte zone in the readout window or in front of the sensor Sensor scanning An interesting application of full control of zone positioning is scanning one or more focused zones in front of a sensor, such as a laser induced fluorescent setup or a impedance sensor. These sensor systems are typical point sensors. However in order to still gather information about zone width, broadening and intensity profiles, the complete zone needs to be "imaged". This can be achieved by controllably moving one or more zones along the sensor window. The procedure can be repeated multiple times in order to increase signal to noise ratio.

Downstream analysis: Selective release can also be used for further downstream analysis of a released compound. An example is the coupling of the channel to a mass spectrometer, e.i. by electrospray injection. The selective release concept enables release of analyte zones one after the other. This zone-by-zone injection reduces risk of interference between various compounds. An example of such interference is ion-suppression in electrospray ionization.

A specific example of this is salt removal in complex biological samples. Salts can be trapped in dzITP zones, while analytes of interes, e.g. hormones or metabolites are continuously released and sent to a down stream detector, optionally concentrated in a second dzITP unit.

The following, non-limiting examples illustrate the process according to the invention. It should be understood, however, that the invention is not limited to the specific details of the Examples.

Experimental Part

Example 1

Chemicals: Lithium carbonate was obtained from Acros Organics (Geel, Belgium), disodium fluorescein was obtained from Riedel-de Haen (Seelze, Germany), 6-carboxyfluorescein was obtained from Sigma-Aldrich (Steinheim, Germany), and sodium acetate was obtained from Merck (Darmstadt, Germany). FITC-labelled amino acids were synthesized as described in the Supporting Information. In all experiments, 2.0 mmol/L lithium carbonate, pH 10.6, was used as the background electrolyte. Solutions were prepared fresh before experiments.

Chip Preparation: Chips were fabricated in Pyrex wafers using standard lithography techniques and deep reactive ion etching (DRIE). The chip fabrication procedure is described in detail in the Supporting Information. The microchannels had 1.7 μm depth and 20 μm width. Microchannel lengths between fluid reservoirs and the nanochannel were 0.91 cm. The nanochannel that connected the two microchannels was 60 nm deep, 25 μm wide, and 50 μm long. The chip was prefilled with ethanol to eliminate air trapping, after which the chip was flushed at least 15 min with 100 mmol/L NaOH, 15 min with demineralised water, and 15 min with background electrolyte (2.0 mmol/L lithium carbonate). Fluid replacement and flushing was accomplished by leaving the fluid reservoir at one end of a microchannel empty. A combination of capillary action and evaporation of fluid generated a flow which was sufficient to replace all fluid in a microchannel in approximately 3 min. Reservoirs were washed 3 times after fluid replacement. After flushing, all channels and reservoirs were filled with the background electrolyte (2.0 mmol/L lithium carbonate).

Setup and Microscopy: Access holes were extended with fluidic reservoirs (volume 100 µL) using a custom-build interface that was attached to the chip surface using a vacuum. The fluidic reservoirs were electrically connected using gold electrodes. Two power supplies (ES 0300 045, Delta Elektronika BV, Zierikzee, The Netherlands) were controlled via the analogue outputs of an NI USB 6221 data acquisition system using LabVIEW 8.2 software (National Instruments, Austin, Tex.). For fluorescence microscopy, an Olympus IX71 microscope (Olympus, Zoeterwoude, The Netherlands) was used in combination with an Hamamatsu Orca-ER digital camera and Hokawo version 2.1 imaging software (Hamamatsu Photonics, Nuremberg, Germany). The magnification was 40. To minimize photo-bleaching, low lamp intensities were combined with 1.0 s integration times.

Data Processing: Spatiotemporal plots (FIG. 6) were composed using MATLAB, by adjoining fluorescence profiles obtained from image sequences that were recorded during the experiments. Fluorescence profiles were obtained by averaging 50 image lines and correcting them for background signal. False colours were assigned to represent fluorescence intensity. Raw CCD images were used in FIG. 3. Fluorescence profiles were obtained from the CCD images and were smoothed by averaging over 5 pixels. Slope values were determined at the inflection points of the smoothed profiles and normalized with respect to the maximum intensity value of the corresponding analyte zone. Locations of the edges of the zones were obtained by determining the position of the inflection point relative to the upstream edge of the nanochannel.

RESULTS AND DISCUSSION

Device Operation: FIGS. 3 a, b shows the general device operation for dzITP. The upper channel in FIGS. 3 a, b is the separation channel; this is the channel where isotachophoretic zones are formed during the experiment. Three-point voltage actuation is utilized: to each of the access holes of the separation channel a voltage source is connected, while the other channel is connected to ground. Upon voltage application, concentration polarization takes place: an ion depletion zone forms in the separation channel, while in the other channel an ion enrichment zone forms (not shown here). Asymmetric voltage application over the separation channel yields an EOF through this channel. The channel arm between the higher voltage and the nanochannel is referred to as the "upstream channel", while the arm between the lower voltage and the nanochannel is referred to as the "downstream channel" (see FIG. 4a). Downstream, the depletion zone continues to grow until the fluid reservoir is reached. This process sometimes appears to lead to fluctuations during the first 30 to 60 s of an experiment. In the upstream direction, depletion zone growth becomes balanced by the opposing EOF. When the downstream depletion zone reaches the outlet, the electrical resistance in this channel reaches a more stable value, resulting in a near-stable position for the upstream depletion zone border. At this border, analytes are focused based on a difference in ion density (for detailed theory, see Zangle et al. 35).

Meanwhile, analyte concentration and separation into adjacent zones is achieved according to isotachophoretic principles (see FIG. 3b). The depletion zone serves here as a terminating electrolyte, and the background electrolyte takes the function of the leading electrolyte. They define the ionic mobility window of analytes that can be focused. The upper boundary of this mobility window is defined by the mobility of the leading ion in the background electrolyte: analytes with higher mobilities will be transported toward the reservoir. The lower boundary depends on the electric field in the depletion zone, which is very high. For example, Kim et al. measured a 30-fold amplified electric field in the depletion zone; see Langmuir 2009, 25, 7759-7765. Only analytes with very low mobilities are transported through this barrier by EOF.

As the current setup is based on a glass chip, the channels have a negative surface charge. Consequently, only anions are focused and separated at the depletion zone border. In order to enable focusing and separation of cations, the surface charge of the device should be reversed by applying a surface coating or by choosing a different substrate.

Figure 4:
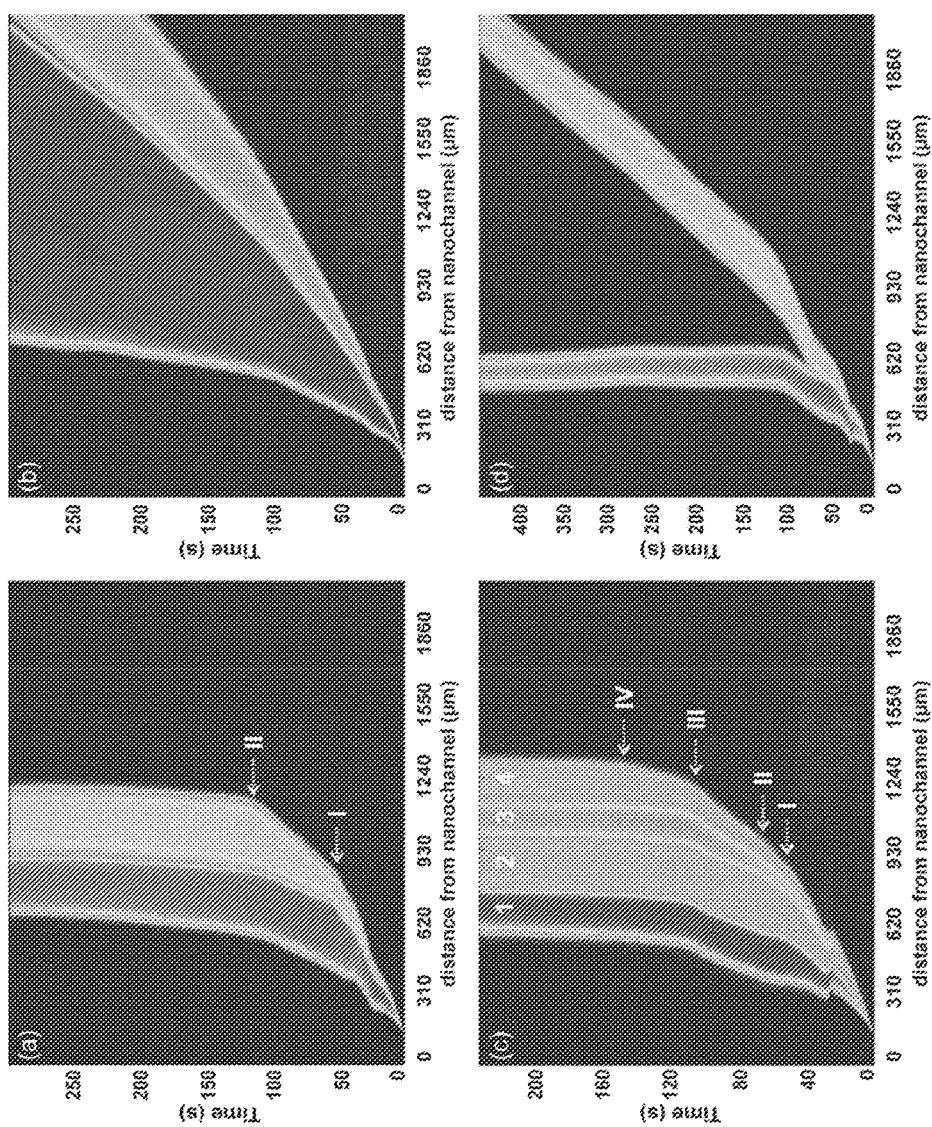
FIG. 4 discloses spatiotemporal plots of dzITP separations: (a) Discrete injection of fluorescein and 6-carboxyfluorescein. Arrows I and II indicate exhaustion of fluorescein and 6-carboxyfluorescein, respectively. (b) Continuous injection of fluorescein and 6-carboxyfluorescein. (c) Discrete injection and separation of four compounds: fluorescein (1), FITC-leucine (2), 6-carboxyfluorescein (3), and FITC-glutamate (4). Arrows I to IV indicate exhaustion of these respective analytes. (d) Discrete injection of fluorescein and 6-carboxyfluorescein combined with a continuous injection of acetate.

Discrete and Continuous Injections: dzITP was demonstrated for both discrete and continuous injections (see FIGS. 4 a, b). Fluorescein, 50 µmol/L, and 6-carboxyfluorescein, 50 µmol/L, were used as analytes; applied voltages were 120 V (upstream) and 40 V (downstream). For discrete injections, only the separation channel was filled with sample, while remaining channels and fluid reservoirs contained background electrolyte only. This resulted in a 309 pL injection volume, as calculated from the microchannel dimensions. FIG. 4a shows that isotachophoretic separation continues until all analytes from the discrete sample are focused, after which the zone widths become constant. Over time, bending points can be observed in the growth rate of the analyte zones, as indicated by the arrows in FIG. 4a. These bending points correspond to the exhaustion of fluorescein (arrow I) and 6-carboxyfluorescein (arrow II). Lower mobility compounds are exhausted at an earlier stage than compounds of higher mobility, the reason being that lower mobility compounds have a lower electrophoretic drift to counter the EOF, resulting in a higher net velocity.

In continuous injections, the analytes were also placed in the upstreamfluid reservoir, providing a practically inexhaustible supply of analytes. Therefore, zone broadening was continuous (see FIG. 4b).

Clearly, no bends due to analyte exhaustion were present. Zone broadening speed of the lower mobility compound (fluorescein) is higher than that of the higher mobility compound (6-carboxyfluorescein), again due to a higher net velocity. Continuous injections are therefore most advantageous for the extraction and focusing of low-concentration, low-mobility analytes, while discrete injections are useful in the quantitative analysis of multiple analytes.

Four-Compound Separation: FIG. 4c shows concentration and separation of four compounds. A discrete sample containing fluorescein, 6-carboxyfluorescein, FITC-leucine, and FITC-glutamate, 40 µmol/L each, was injected. External voltages were 120 V (upstream) and 40 V (downstream). Within 100 s, four zones of clearly distinguishable fluorescence intensity were formed. Standard addition was used to assign the four zones to each of the four analytes: a doubled concentration of the respective analyte led approximately to a doubling of the width of the corresponding zone (see Supporting Information, FIG. 4). Here, too, bends in the profile coincide with the exhaustion of each of the respective analytes.

Use of Spacer Compounds: A combination of a continuous and a discrete injection is shown in FIG. 4d. The upstream fluid reservoir was filled with electrolyte containing 100 µmol/L sodium acetate as a spacer compound, but no analytes. The separation channel was filled with electrolyte containing 30 µmol/L of both fluorescein and 6-carboxyfluorescein as analytes, but no spacer compound. External voltages were 120 V (upstream) and 40 V (downstream). Initially, fluorescein and 6-carboxyfluorescein are focused in adjacent zones. After 70 s, acetate, which has an ionic mobility in between that of fluorescein and 6-carboxyfluorescein, arrives and spaces the two compounds. The fluorescein zone remains focused at the depletion zone border, while the 6-carboxyfluorescein zone is pushed away in upstream direction by the continuously broadening acetate zone.

Spacer addition enables baseline separation of fluorescent compounds enabling more precise identification and quantification. Furthermore, a single compound or a specific group of compounds can be selectively transported away from the depletion zone and can eventually be eluted from the system, while other compounds remain at their near-stationary position at the border of the depletion zone. Advantageously, all compounds remain focused during this process. Thus, spacer addition is a powerful method for purification and transport. Positional Stability. A crucial feature of dzITP is the positional stability of the depletion zone border. A near-stationary condition is reached after a rather short period, typically on the order of 100 s (see FIG. 4), in which depletion rate and EOF velocity reach a balance. A discrete injection experiment was performed with 50 µmol/L of both fluorescein and 6-carboxyfluorescein; external voltages were 120 V (upstream) and 40 V (downstream). In this experiment, the depletion zone border shifted less than 700 µm in 1 h.

A previous report on nanofluidic concentration devices indicated a near-zero shift after 3 h of actuation, see Wang, Y.-C. et al., Anal. Chem. 2005, 77, 4293-4299, although under different experimental conditions, indicating that the result reported here may be further optimized. However, the near-stability of the isotachophoretic separations demonstrated here greatly enhances monitoring of focusing and separation processes by microscopy without x/y control of the microscope stage. Additionally, the experimental time range is much larger than for non-stationary ITP methods, allowing higher concentration factors to be achieved.

Figure 5:
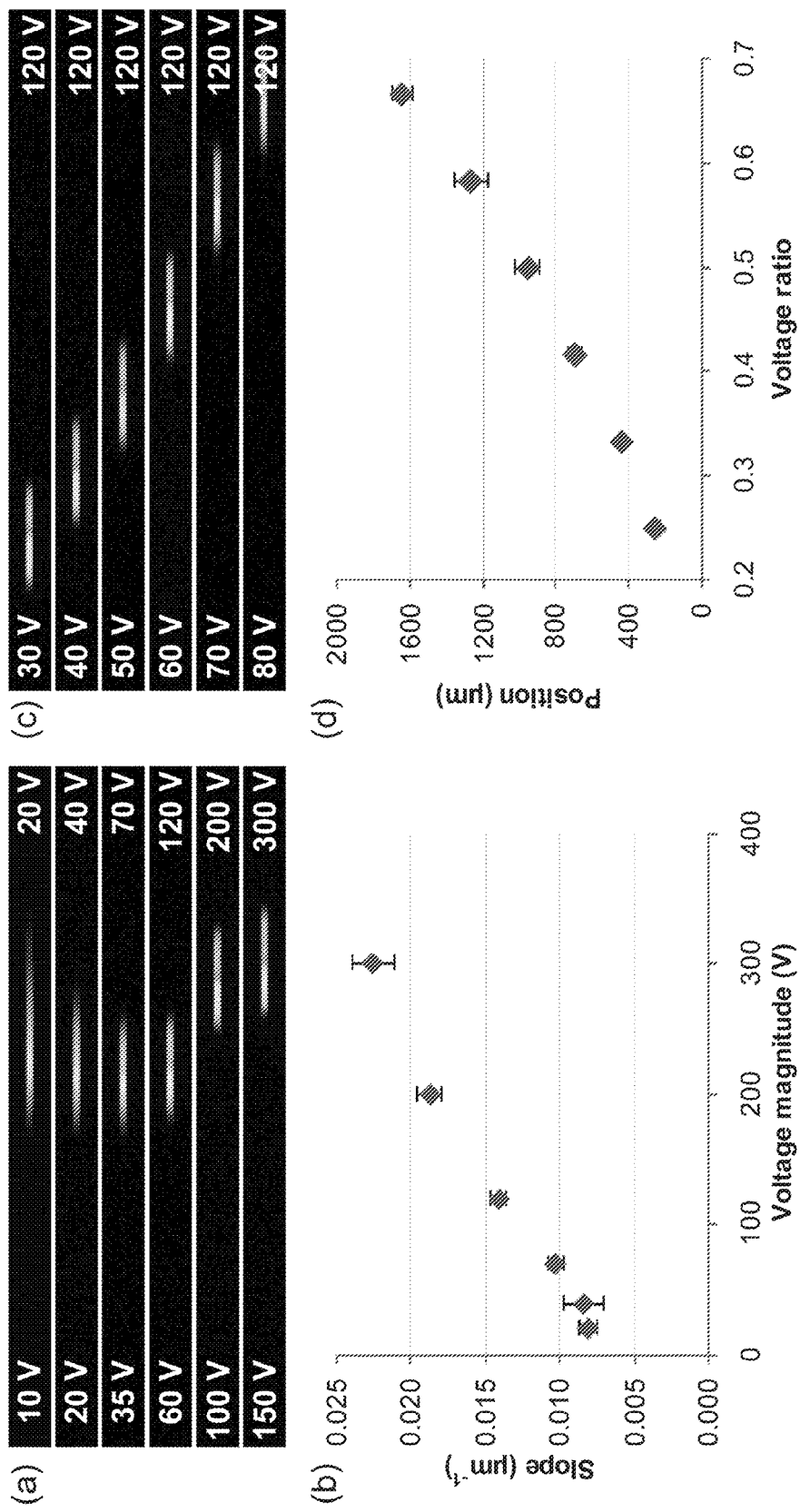
FIG. 5 (a) to (d) discloses a preferred embodiment of the device.

Three-Point Voltage Actuation: In FIG. 5 applicants demonstrate the versatility that is provided by a three-point voltage actuation approach. In FIGS. 5 a,b the magnitude of the upstream and downstream voltages was varied, while maintaining the ratio between them. This enables tuning of the extent to which analytes are focused. For low voltages the two zones are barely distinguishable, while for high voltages sharp edges of the zones can be observed. FIG. 5 b shows normalized slope values in fluorescence intensity per micrometer. The results suggest a linear trend between voltage magnitude and zone sharpness. Analyte zone positions are not greatly influenced by a change of the voltage magnitude as long as the ratio between upstream and downstream voltages is kept constant. In principle, this enables a free choice of the maximum field strength and resulting focusing strength. However, small shifts in analyte zone positions are observed at higher voltage magnitudes. We measured maximum shifts of 364 (21 µm. In FIGS. 5 c,d the voltage ratio is varied by means of the downstream voltage. The zones can be shifted over a range of 1.4 mm by varying the voltage ratio between 0.25 and 0.67 (downstream voltage: upstream voltage). Zone positions appear to relate rather linearly to the voltage ratio. Separations are maintained, although at increasing ratios defocusing occurs. The 1.4 mm zone shift is accompanied by a decrease of slope values on the order of 0.006 $\mu m^{-1}$.

Complete control over analyte zone position and sharpness is a crucial and unique advantage of dzITP over conventional ITP methods. In conventional methods, a single stable position can be obtained by EOF balancing, but during the experiment this position can not be easily changed without changing parameters like pH or electrolyte concentrations. Contrarily, in dzITP this is easily done by tuning the upstream and downstream voltage magnitudes. Real-time image analysis of fluorescent markers can be used as feedback input for three-point voltage actuation, enabling automated zone positioning control. Moreover, great benefit is offered to experimental readout, as analyte zones can be scanned in a precisely controllable manner by steering them along a sensor.

Synergy of dzITP: dzITP provides synergies that emerge from the combination of ITP and nanofluidic concentration devices, as provided by dzITP. Except for the requirement of multiple electrolytes, dzITP has all key characteristics of ITP: focusing toward plateau concentrations and separation into adjacent zones that are ordered according to ionic mobility. Spacer compounds may be used to segregate adjacent zones. From nanofluidic concentration devices, dzITP takes the single electrolyte advantage, as well as positional stability. Three-point voltage actuation adds to this synergy the possibility of precise control of focusing strength and zone positioning.

Applicants have demonstrated isotachophoretic separations employing a nanochannel-induced depletion zone as a trailing electrolyte. dzITP requires only a single electrolyte to be injected and can be performed easily with both discrete and continuous injections. We demonstrated separations of up to four compounds in clearly distinguishable zones within 100 s. A spacer was inserted to improve baseline separation of fluorescent compounds, and to induce selective transport of analytes while maintaining sharply focused zones. Moreover, full control over analyte position and zone sharpness was demonstrated using the unique three-point voltage control of dzITP. Scanning of analyte zones using three-point voltage actuation will enable simple integration of sensors such as surface-enhanced Raman spectroscopy (SERS), surface plasmon resonance (SPR), and conductimetry or electrochemical detection. As dzITP is much easier to use than conventional ITP, integration into a microfluidic platform for everyday laboratory use will be very attractive, as exemplified by the Agilent 2100 Bioanalyzer for on-chip capillary electrophoresis. Integration in hand-held analysis devices, as has been recently done for conventional ITP, see Kaigala, G. V. et al., Lab Chip 2010, 10, 2242-2250, may find interesting applications in water quality monitoring, explosive detection, point-of-care screening, etc. Future research focuses on coupling of the technique to sampling and detection modules. We see great potential for dzITP in our metabolomics research, particularly for the extraction, preconcentration, and quantification of low-abundant metabolites from small complex biological samples. Thanks to its unique combination of voltage-controlled versatility and single-electrolyte simplicity, dzITP holds the promise to become a core component in the electrokinetic chip-based platforms of the future.

Example 2

Chips, Setup and Microscopy were as in Example 1. In most experiments, current actuation was performed via the electrode connected to the upstream (sample) reservoir, while the downstream reservoir was connected to a constant voltage. In these experiments, only one of the reservoirs of the bottom channel was connected to ground (see FIG. 5a). However, the pulsed mode experiments (FIG. 6), both the upstream and downstream reservoir were connected to voltage sources, while both reservoirs of the bottom channel were connected to ground. For imaging, we used a fluorescence microscope (Olympus IX71, Olympus, Zoeterwoude, The Netherlands) to which a Hamamatsu Orca-ER digital camera was mounted, which was controlled by Hokawo version 2.1 imaging software (Hamamatsu Photonics, Nueremberg, Germany). The integration time for an image was 0.5 s (1 s in FIG. 7), and the magnification was 40×. Raw CCD images were used in the figures. Fluorescence intensity values were obtained by averaging 50 image lines, corrected for background signal. Urine Analysis. Urine was obtained from a male volunteer, and 100× diluted in 2.5 mmol/L lithium carbonate containing 150 µmol/L of fluorescein. No further sample preparation was done before injection of the sample into the device.

Figure 6:
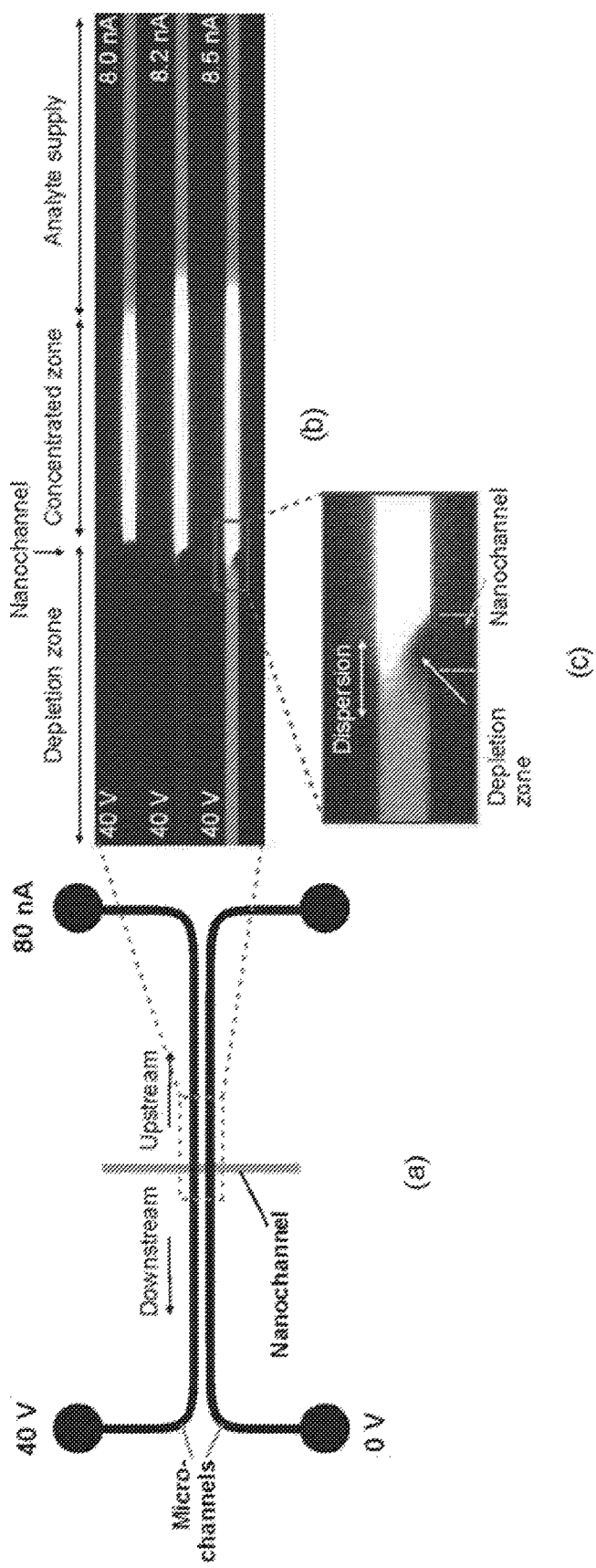
FIG. 6(a) to 6(c) discloses a three-point voltage actuation.
Figure 7:
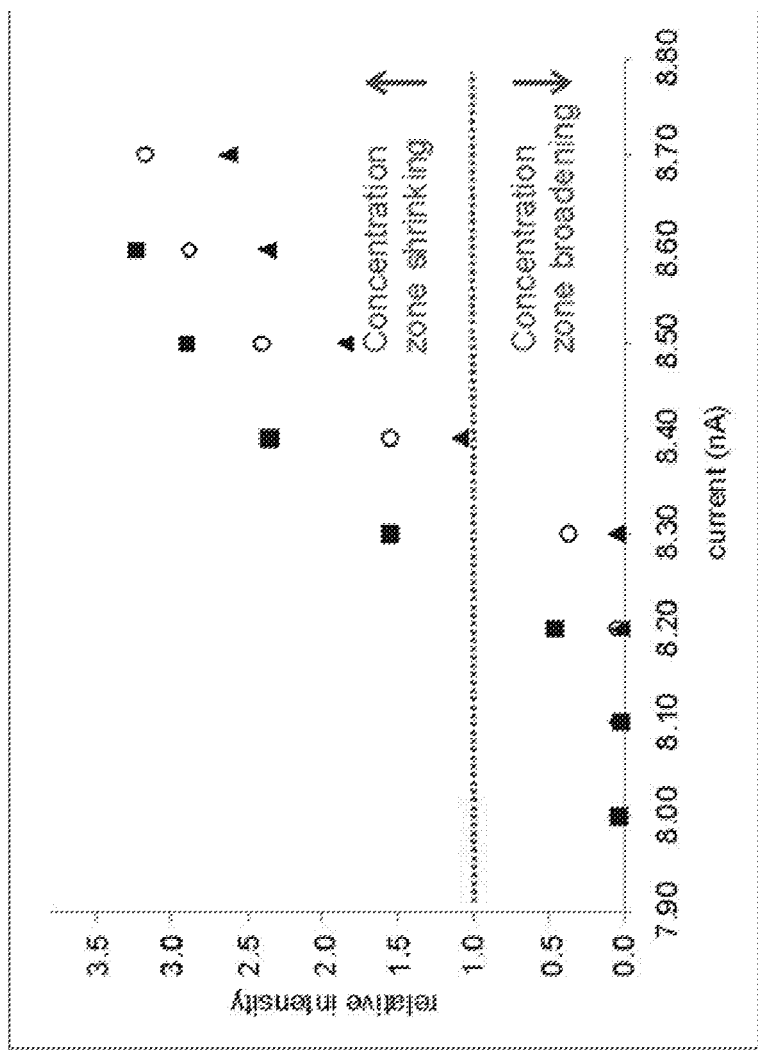
FIG. 7 discloses a graph of fluorescence intensity in the downstream channel versus the applied current. The results of three experimental series with identical experimental conditions are shown to indicate reproducibility. The red line indicates the balance between concentration zone growth and release. Below this line the zone is broadening, above it is shrinking. Note: the x-axis does not start at zero.

Results and Discussion:

Analyte Release: The filter is enabled by the fact that analytes in dzITP zones can be released along the depletion zone into the downstream part of the separation channel, as shown in FIG. 6. A depletion zone is formed in the separation channel upon voltage actuation. The analyte, 150 µmol/L of fluorescein, is focused at the upstream border of the depletion zone and forms an isotachophoretic zone. 2.5 mM lithium carbonate was used as the electrolyte. The fluorescein zone could be positioned at varying distances from the nanochannel by changing the ratio between the voltages and/or currents at the upstream and downstream fluid reservoirs. This positioning is the result of a shift in balance between nanochannel ion pumping and electroosmotic flow (EOF). Increasing the currents at the upstream reservoir results in increased EOF; therefore the fluorescein zone is positioned closer to the nanochannel. In FIG. 6b, three situations are shown. When 8.0 nA is applied, the fluorescein zone is positioned at a small distance from the nanochannel junction. Upon a small increase in EOF (by increasing the current to 8.2 nA) the depletion zone cannot be maintained any longer in the upstream channel. A small stream of non-depleted fluid from the upstream channel, which carries the analytes, starts to flow into the downstream channel. In fact, at the nanochannel junction two laminar streams can be discerned, one containing ion-rich fluid from the upstream channel and one containing ion-depleted liquid resulting from the concentration polarization process over the nanochannel (FIG. 6c). Downstream from the nanochannel, the two streams rapidly mix through dispersion, forming a homogeneous dilution of the released analytes. After increasing the current further to 8.5 nA, the contribution of the fluorescein-rich fluid stream becomes much larger, resulting in a corresponding increase in the fluorescence intensity in the downstream channel. The graph in FIG. 7 shows how the intensity of released fluorescein in the downstream channel depends on the applied current. A zone of concentrated fluorescein was established by conventional dzITP and subsequently released using different currents on the sample reservoir, while maintaining a constant voltage of 40V at the downstream reservoir. The results of three experimental series using the same conditions are shown, to indicate reproducibility. For each series, a threshold current can be derived from the graph. We defined the threshold current as the value for the current at the upstream fluid reservoir at which the analyte starts to be released (given a constant voltage at the downstream fluid reservoir). In the graph, these threshold currents also can be estimated by interpolation of the point where fluorescence intensity becomes zero. These estimated values vary in the order of 2.5%. Even though between the experimental series the variation in threshold currents is quite small, the corresponding variations in fluorescence intensity are significant. The reason is that in the filter regime the amount of analyte that is released is quite sensitive to small changes in electric fields. There are several potential causes for small variations in threshold currents, most importantly a shift in electrolyte distribution within the nano/microchannel network. Additional effects include conductivity and pH changes due to $CO_2$ dissolution from the atmosphere and variations in the zeta potential of the micro- and nanochannel walls. To obtain better reproducibility, applied currents settings should therefore be corrected for the threshold current. In FIG. 7, the values for the fluorescence intensities in the downstream channel are calculated relative to the intensity in the channel region upstream from the concentrated zone. Therefore, if the relative intensity is equal to one, supply and release of analytes are equal. This particular regime is indicated by the red dashed line in FIG. 7. At higher values, more analyte is released than supplied and concentrated analyte zones will shrink and ultimately disappear. At lower values, release is smaller than supply and concentrated zone continue to grow.

Figure 8:
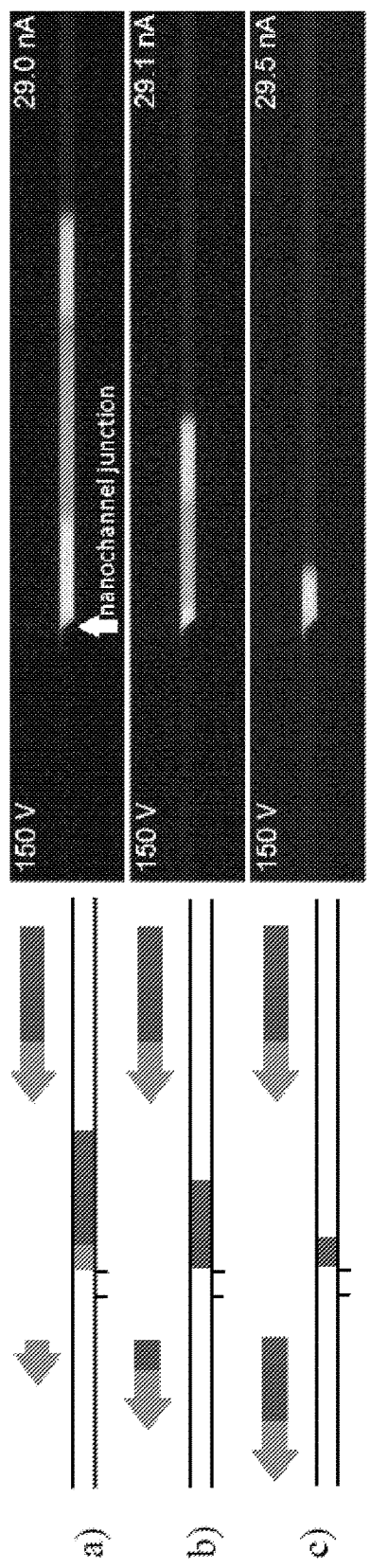
FIG. 8 discloses a schematic representation (left) and experimental results (right) showing continuous operation of the dzITP filter. The filter is tuned by balancing release (left arrows) and supply (right arrows) of analytes, determining which analytes pass through the filter and which are trapped in isotachophoretic zones. Analytes are fluorescein, FITC-leucine and 6-carboxyfluorescein. a) Fluorescein is partly released, the other analytes are completely retained. b) Fluorescein is completely released, FITC-leucine partly. c) Fluorescein and FITC-leucine are completely released, 6-carboxyfluorescein partly.

Continuous Filtering: FIG. 8 shows how the dzITP filter is operated in order to collect compounds above a certain mobility cut-off while continuously releasing other compounds. In this experiment, fluorescein, 6-carboxyfluorescein and FITC-leucine, each 50 µmol/L, were injected continuously by placing the sample solution in the upstream reservoir. A depletion zone was established and subsequently the current that was applied through the upstream reservoir was tuned just above the threshold current (FIG. 8a). This resulted in continuous release of analyte along the depletion zone. The flux of released analyte that was released was smaller than the flux of fluorescein that was supplied. Therefore, fluorescein was only partly released, while the concentrated zone continued to broaden. The other two analytes focused in zones behind the fluorescein zone and therefore were not released at all (FIG. 3d). This condition can be written as general formula III $$0 < J_{release} < J_{fluorescein} \quad (III)$$

where $J_{release}$ and $J_{fluorescein}$ are the fluxes (in mol/s) of released analyte and supplied fluorescein, respectively. When increasing the current, more fluorescein is released than supplied; therefore no fluorescein zone is formed.

Additionally, part of the FITC-leucine is released. Because release of FITC-leucine is only partial, a FITC-leucine zone is still formed, behind which all of the 6-carboxyfluorescein is collected in a second zone (FIG. 8b). This filtering condition can be written as general formula (IV):

$$J_{fluorescein} < J_{release} < (J_{fluorescein} + J_{FITC-leucine}) \quad (IV)$$

In this filtering regime still a narrow bright band can be observed at the depletion zone border, presumably this is due to stacking of fluorescein. However full release of fluorescein is evidenced by the fact that this band does not broaden over time. Moreover, the FITC-leucine zone is growing less rapidly, which is the evidence of partial release of FITC-leucine. This is only possible if all fluorescein is released. A third regime is shown in FIG. 8c, in which all FITC-leucine (together with all fluorescein) and part of the 6-carboxyfluorescein is released. Here, the filtering condition is (V):

$$(J_{fluorescein} + J_{FITC-leucine}) < J_{release} < (J_{fluorescein} + J_{FITC-leucine} + J_{6-carboxyfluorescein}) \quad (V)$$

Finally, at sufficiently high current, no filtering and no zone formation is observed yielding the condition (VI):

$$J_{release} > (J_{fluorescein} + J_{FITC\text{-}leucine} + J_{6\text{-}carboxyfluorescein}) \qquad (VI)$$

In this regime, the electrolyte is co-released with all the analytes. The continuous filtering mode can be automated by setting the zone width of a specific, continuously injected "marker compound" to a predefined value, using a real-time image analysis algorithm as a feedback for applied voltages and currents. Such a procedure implies partial release of the marker compound.

The ionic mobility of the marker compound precisely defines the ionic mobility cut-off of the dzITP filter: isotachophoretic principles guarantee that all ions with lower mobilities than the marker compound will be co-released while all higher mobility compounds will be focused and separated adjacent to the marker zone.

The dzITP filtration is based on release along the depletion zone, yielding a temporary two-stream profile of analyte and depletion zone (see FIGS. 6 c and d). This mechanism is in contrast with another mechanism, in which compounds are released through the depletion zone. Release through the depletion zone occurs when the contribution of electrophoretic drift of compounds in the depletion zone is smaller than the electro-osmotic flow. This occurs for compounds with low ionic mobilities first. This mechanism is a probable explanation for the ion-selectivity observed in electro-capture devices, in which peptides and other compounds could be released sequentially across enrichment and depletion zones formed by concentration polarization.

However, as the electric field in the depletion zone is in the order of 30× higher than in the background electrolyte, this approach seems not suited to discriminate between metabolites, which mostly have only 1-4× lower mobility than the background electrolyte. As dzITP filtering does not depend on the electric field in the depletion zone, it yields a much better controllable filtering approach, particularly for the sample preparation of metabolites.

Figure 9:
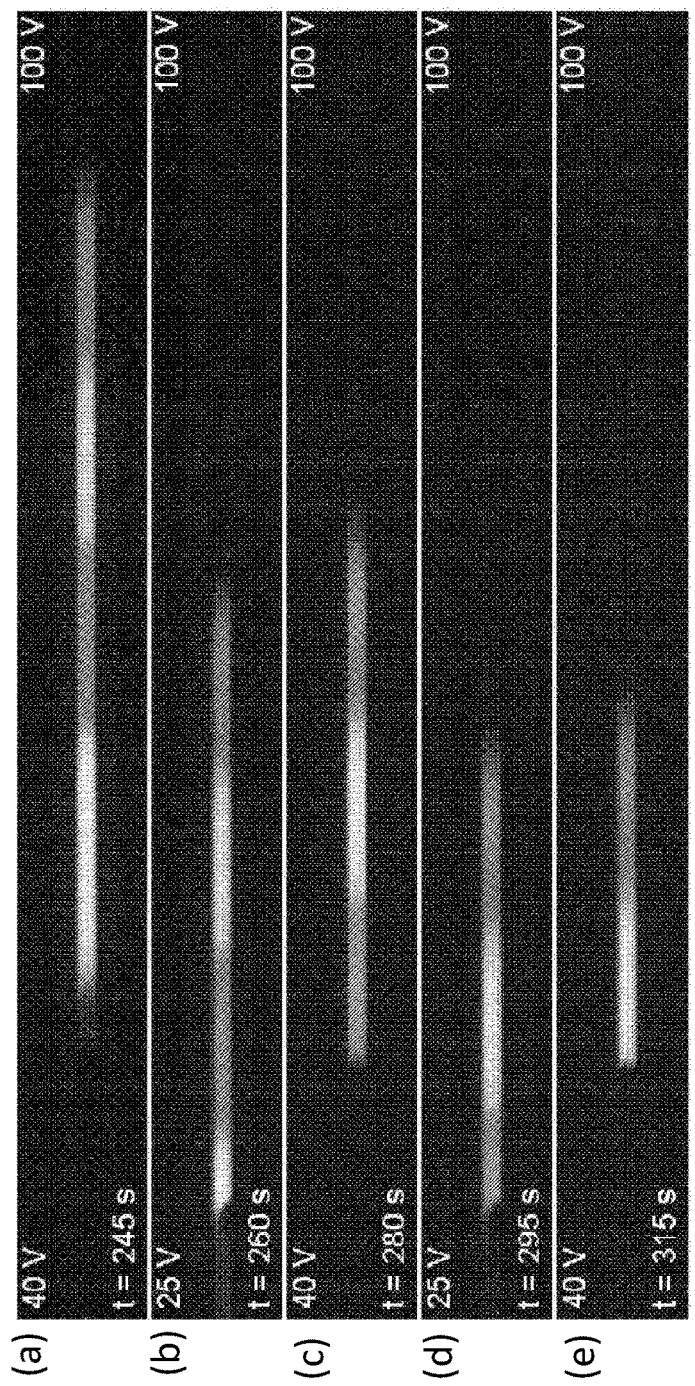
FIG. 9(a) to 9(e) discloses the pulsed operation of the dzITP filter.

Pulsed Filtering: FIG. 9 shows dzITP filtering in pulsed mode. A discrete amount of fluorescein (60 μmol/L), 6-carboxyfluorescein, FITC-leucine, and FITC-glutamate, (each 30 μmol/L) was injected by filling the separation channel with electrolyte plus sample solution, while the upstream "sample" reservoir contained electrolyte without sample. First, a depletion zone was established in the upstream part of the channel, at the border of which the analytes were focused. Fluorescein focused closest to the depletion zone border, followed by FITC-leucine, 6-carboxyfluorescein and finally FITC-glutamate. During this stage, applied voltages were 120 V (upstream) and 40 V (downstream). After 3 minutes of voltage actuation, the dzITP separation was completed, resulting in the starting situation for the pulsed release of compounds (FIG. 9a). The downstream voltage was temporarily lowered to 25 V. The analyte zones were transported into the downstream direction until the nanochannel junction was reached, after which the first analyte zone (fluorescein) started to be released (FIG. 9b). Although in isotachophoretic separations different analyte zones have different electric fields, the device appeared to be insensitive to this. Therefore, all analyte zones would have been released if the downstream voltage were maintained at a lowered value. To prevent this, the downstream voltage was increased again to 40 V after the fluorescein zone was released. The depletion zone was re-established rapidly (sub-second scale), and the upstream depletion zone border then moved to its original position slowly (~30 seconds). Behind the depletion zone border, the remaining analyte zones were retained (FIG. 9c). This procedure was subsequently repeated twice to release the FITC-leucine (FIGS. 9d, e) and 6-carboxyfluorescein zones individually. In this experiment, the voltage actuation steps that ended the release of an individual zone were performed manually, based on visual identification of zone position. Voltage actuation based on feedback from automatic image analysis might yield a more reliable procedure. It should be taken into account that in isotachophoretic separation there is always overlap between neighbouring zones due to diffusion. Several approaches to this problem can be envisioned.

First, if one desires "pure" analyte, excluding other dzITP-separated compounds, only the heart of the corresponding zone can be selected. Second, if one wants to ensure to select all of a certain zone, the "cuts" can be made in the centres of the neighbouring zones. Finally, analytes can be released with regular time intervals to fractionate the dzITP-separation while accepting that a single compound might appear in multiple fractions, or that a single fraction contains multiple compounds.

Figure 10:
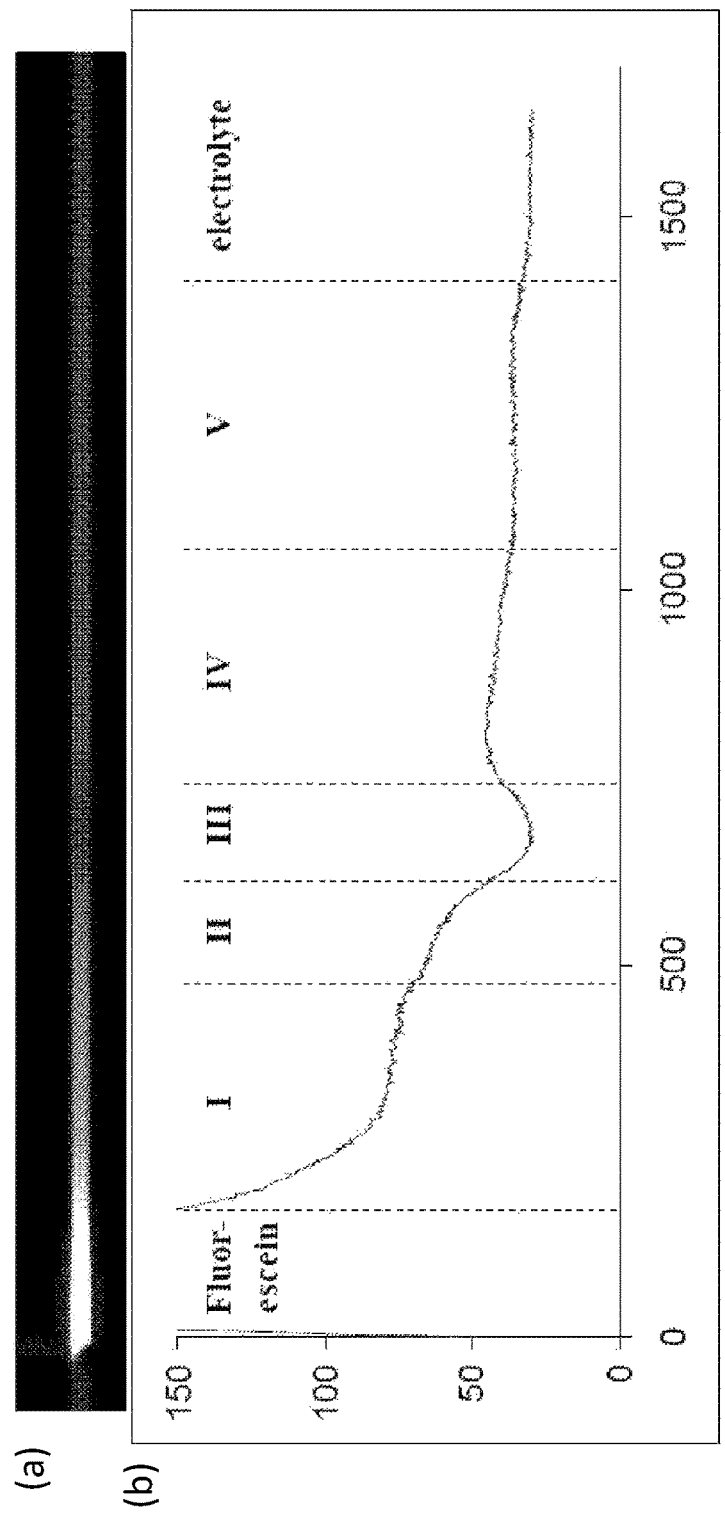
FIG. 10(a) shows a CCD image showing dzITP filtration of urine after a period of time of actuation, using partly released fluorescein as a marker for ionic mobility cut-off and for indirect detection.
FIG. 10(b) shows a fluorescence profile of the CCD image showing five putative analyte zones.

Urine Sample: FIG. 9 shows a proof of principle for the application of the dzITP filter to a complex biological sample, using fluorescein as a marker compound. A continuous low-pass dzITP injection was performed. Without low-pass filtering, fluorescein and undesired low-mobility compounds would accumulate, rapidly swamping the complete read-out window. Therefore, voltages were tuned such that a fluorescein zone was established with an approximately stable width. Behind this fluorescein zone, compounds from the urine sample formed several other zones (FIG. 10a). The zones are visualized by indirect detection. In isotachophoretic separations, each zone has its specific conductivity. The continuously injected fluorescein travels through these zones and co-adjusts its concentration to the local conductivity.

The fluorescein thus is not only used as a marker, but also acts as tracer; (a so-called "underspeeder"). In the fluorescence profile in FIG. 10b, five putative analyte zones are indicated. As in each isotachophoretic separation, the zones have overlap at the borders. The putative zone borders are therefore indicated at the inflection points between the zones in the fluorescence profile. Theoretically, with this mode of indirect detection a staircase-like fluorescence profile is expected, with increasing fluorescence intensities for each zone closer to the fluorescein zone.

However, zone III in FIG. 10b has significantly lower fluorescence intensity. Possibly, this zone contains an analyte which quenches fluorescence.

The identity of the detected analytes was not determined in the experiment. However, the fluorescein marker and the carbonate electrolyte define a window of ionic mobilities, which contains only a limited number of metabolites out of the thousands of compounds in urine. These probably include only very small molecules or molecules that have, like fluorescein, at least a doubly negative charge.

Notable metabolites that fulfil these conditions include acetate, aspartate, glutamate and several citric acid cycle products. The carbonate electrolyte defines the upper limit of the mobility window and excludes some small ions, particularly chloride. Low-mobility compounds are co-released with the fluorescein. It is probable that more than five urine metabolites are retained in the dzITP zones, however they might have very low concentrations and therefore are not forming individual zones, but rather focused in non-detectable peaks between the zones. For sample analysis it is therefore desirable to continue this continuous filtration step with a number of pulsed releases as described above. This way, fractions of enriched analytes can be sent to a detector located along the downstream channel for identification and quantification.

For metabolomics research, the dzITP filter will be highly enabling, because it can be used to remove at least two undesired classes of compounds from ultra-small complex samples: proteins, which have lower mobility, and salts, which have higher mobilities than most metabolites.

Preferably, a device with two dzITP filters in series is employed, wherein salts can be trapped in the first filter, and metabolites in the second filter, while proteins are removed.

Example 2 illustrates the potential of the dynamic low-pass filter that separates compounds based on ionic mobility according to a preferred embodiment of the invention.

The dzITP filter advantageously works by voltage or current-controlled release of compounds along a nanochannel-induced depletion zone.

Isotachophoretic separation of compounds before the filter results in selectivity.

In pulsed mode, dzITP-separated compounds are fractionated in plugs that are released sequentially along the depletion zone.

In continuous mode, a certain (marker) compound may be partially released, whereby the ionic mobility of this compound defines the cut-off of the filter. Compounds with lower mobility are co-released, compounds with higher mobility are trapped in isotachophoretic zones. Importantly, this cut-off can be simply and rapidly tuned by voltage or current actuation. This in contrast to many other filtering techniques, which require modification of chemical or physical properties for tuning.

The dzITP filter has been demonstrated with diluted raw urine sample, using fluorescein as a marker. Out of the thousands of compounds in urine, a small ionic mobility window was selected wherein five analyte zones were indirectly detected. The dzITP filter can thus enrich specific compounds from complex biological samples and enable real-time monitoring and detection.

The invention claimed is:

1. A method for concentrating, separating and/or isolating a plurality of charged analytes contained in a sample by depletion zone isotachophoresis comprising:
   (i) introducing the sample into an electrolyte, in an apparatus comprising at least a main separation channel (C) comprising the electrolyte, the channel (C) comprising a downstream end (D) and an upstream end (U), and a depletion zone formation means (N) placed in or connected to an intermediate region between the upstream end and the downstream end, at an upstream channel region adjacent to the upstream end (U), and
   (ii) forming and/or maintaining an ion depleted zone in both the separation channel (C) and adjacent to the depletion zone formation means at a depletion rate (R) using the depletion zone formation means, and
   (iii) applying an electric field (E1) between the downstream end (D) and the upstream end (U) and applying a downstream fluid flow (F), thereby causing focussing and separation of the analytes forming respective focused analyte zones in the separation channel (C) and adjacent to the ion depleted zone, and
   (iv) adjusting depletion rate (R) and optionally fluid flow (F) to move at least one focussed analyte zone in a upstream and/or downstream direction and/or position the one or more focussed analyte zones at a desired position in the separation channel (C).

2. The method according to claim 1, wherein a second electric field (E2) is present across the depletion zone formation means (N) that controls the depletion rate (R) and/or the position of at least one focussed analyte zone.

3. The method according to claim 1, wherein the depletion zone formation means (N) is
   (i) a perm selective membrane, nanopore, or nanochannel, and wherein formation of the ion depleted zone is induced by ion concentration polarization; or
   a nanochannel fluidically connecting the upstream and the downstream end of channel (C).

4. The method according to claim 1, wherein the longitudinal flow (F) is an electro-osmotic flow, a pressure driven flow, or a combination thereof.

5. The method according to claim 1, wherein step (iv) includes varying the electric field (E1) and/or (E2), and/or varying the pressure driven flow.

6. The method according to claim 1, wherein at least one of the following occurs:
   (a) the electrical field (E1) and/or (E2) are controlled by current or voltage sources or a combination thereof, preferably by applying a three point voltage difference over the device;
   (b) the presence or absence of a focussed analyte and/or the instant concentration thereof is detected electrically, thermally or optically in (iii) or
   (c) detecting the position and/or composition of the focused zones.

7. The method according to claim 6, wherein the electrical detection is done by a measuring a current or resistance plateau, or wherein the optical detection is done by fluorescence, emission or absorption spectroscopy.

8. The method according to claim 1, wherein the sample contains at least a first and a second analyte, which are focussed and separated, and wherein the first analyte is positioned downstream relative to the second analyte, the method further comprising the step of adjusting the position of the second analyte such that the first said analyte zone is transported partly or entirely into a downstream direction along the ion depleted zone.

9. The method according to claim 8, wherein the first analyte is:
   (a) a marker molecule suitable for direct or indirect detection, a reaction product, and/or an abundant compound; and/or
   (b) is transported to a detection means for further analysis, including but not limited to mass spectroscopy, Raman, IR spectroscopy; or to a recovery chamber, such as an assay chamber, or a collection chamber.

10. The method according to claim 1, wherein the position or composition, or both, of at least one focussed analyte zone or border thereof is detected by a sensor.

11. The method according to claim 10, wherein the sensor is part of a control system that measures and adjusts the position of at least one analyte zone or border thereof.

12. The method according to claim 11, wherein the control system comprises a feedback control loop.

13. The method according to claim 1, wherein the device comprises fluid connections to one or more additional channels for analyte recovery or introduction of compounds, preferably spacer compounds, other electrolytes, reactants, marker compounds; and/or for the removal of dyes, salts, reaction products, proteins, other interfering compounds; and/or for the recovery of analytes.

14. The method according to claim 1, comprising employing a device comprising multiple depletion zone formation means.

15. The method according to claim 1, wherein an extraction channel (E) is provided at a junction with the downstream end of the channel (C) being transversely oriented in respect of the main separation channel (C) and having an extraction part leading out of the main separation channel; and wherein a transversal flow is applied when an focussed analyte band has reached the junction between channel (C) and the extraction channel (E).

16. The method according to claim 1, wherein additionally to sample, one or more spacer compounds (S) are present.

17. An apparatus for preconcentrating and isolating a plurality charged analytes contained in a sample by depletion zone isotachophoresis, comprising:
(a) a main separation channel (C) comprising an electrolyte, the channel (C) comprising an upstream end (U) and a downstream end (D), and
(b) a depletion zone formation means (N) placed in an intermediate region between the Upstream end and the Downstream end;
wherein the apparatus is configured to adjust depletion rate (R) and optionally fluid flow (F) to move at least one focussed analyte zone in a upstream and/or downstream direction and/or position the one or more focussed analyte zones at a desired position in the separation channel (C).

18. The apparatus according to claim 17, further comprising one or more of:
(c) an extraction channel (E) having a junction with the main channel at the downstream side of the depletion zone formation means (N), being transversely oriented in respect of the main separation channel (C) and having an extraction part leading out of the main separation channel,
(d) means for introducing a sample into an internal segment of the main separation channel located between the upstream end (U) and the downstream end (D),
(e) means for applying a first electric field (E1) between the upstream end (U) and the downstream end (D), and
(f) means for applying a second electric field (E2) over the depletion zone formation means (N);
(g) means for applying a flow along the longitudinal direction along the main separation channel; and
(h) a means for detecting focused spacer zones and/or focused analyte zones within the separation channel (C) and/or the depletion zone formation means (N).

19. The apparatus according to claim 18, wherein at least one of the following is present;
(i) the depletion zone formation means (N) is a nanochannel fluidically connecting the downstream and the upstream end of channel (C); or
(ii) the extraction channel (E) comprises a collection zone located at an end of the extraction part thereof, and/or a means for varying the electric field (E1) and/or (E2), and/or varying the pressure driven flow; or
(iii) the extraction channel (E) further comprises an injection part leading into the main separation channel for administering a transversal flow.

* * * * *